(12) United States Patent
Jourdier et al.

(10) Patent No.: US 10,787,655 B2
(45) Date of Patent: Sep. 29, 2020

(54) PROCESS FOR THE PRODUCTION OF OLIGOSACCHARIDES FROM LIGNOCELLULOSIC BIOMASS

(71) Applicants: IFP ENERGIES NOUVELLES, Rueil-Malmaison (FR); ARGO INDUSTRIES RECHERCHE ET DEVELOPPEMENT, Pomacle (FR); INSTITUT NATIONAL DE LA RECHERCHE AGRONOMIQUE, Paris (FR)

(72) Inventors: Etienne Jourdier, Vaucresson (FR); Caroline Aymard, Lyons (FR); Fadhel Ben Chaabane, Paris (FR)

(73) Assignees: IFP ENERGIES NOUVELLES, Rueil-Malmason (FR); INSTITUT NATIONAL DE LA RECHERCHE AGRONOMIQUE, Paris (FR); ARGO INDUSTRIES RECHERCHE ET DEVELOPPEMENT, Pomacle (FR)

( * ) Notice: Subject to any disclaimer, the term of this patent is extended or adjusted under 35 U.S.C. 154(b) by 796 days.

(21) Appl. No.: 14/654,063

(22) PCT Filed: Nov. 18, 2013

(86) PCT No.: PCT/FR2013/052772
§ 371 (c)(1),
(2) Date: Jun. 19, 2015

(87) PCT Pub. No.: WO2014/096586
PCT Pub. Date: Jun. 26, 2014

(65) Prior Publication Data
US 2015/0344856 A1     Dec. 3, 2015

(30) Foreign Application Priority Data
Dec. 20, 2012  (FR) ..................... 12 03536

(51) Int. Cl.
| | |
|---|---|
| *C12N 9/24* | (2006.01) |
| *C12P 7/04* | (2006.01) |
| *C12P 7/28* | (2006.01) |
| *C12P 19/12* | (2006.01) |
| *C12P 7/10* | (2006.01) |
| *C12P 7/16* | (2006.01) |
| *C12P 21/00* | (2006.01) |
| *C12N 9/42* | (2006.01) |
| *C12P 19/00* | (2006.01) |

(52) U.S. Cl.
CPC ......... *C12N 9/2402* (2013.01); *C12N 9/2437* (2013.01); *C12P 7/04* (2013.01); *C12P 7/10* (2013.01); *C12P 7/16* (2013.01); *C12P 7/28* (2013.01); *C12P 19/00* (2013.01); *C12P 19/12* (2013.01); *C12P 21/00* (2013.01); *C12P 2203/00* (2013.01); *C12Y 302/01004* (2013.01); *Y02E 50/10* (2013.01); *Y02E 50/16* (2013.01)

(58) Field of Classification Search
CPC .. C12P 19/12; C12P 21/00; C12P 7/10; C12P 7/16; C12P 19/00; C12P 7/04; C12P 7/28; C12P 2203/00; C12N 9/2437; C12N 9/2402; C12Y 302/01004; Y02P 20/52; Y02E 50/10; Y02E 50/16
USPC ................ 435/100, 150, 157, 160, 165, 209
See application file for complete search history.

(56) References Cited

U.S. PATENT DOCUMENTS 7,781,191 B2 * 8/2010 Dunson, Jr. ............... C12P 5/00
426/7

OTHER PUBLICATIONS

Knutsen et al. Cellulase Retention and Sugar Removal by Membrane Ultrafiltration During Lignocellulosic Biomass Hydrolysis. Applied Biochemistry and Biotechnology (2004), v113-116, p. 585-599.*
Lloyd et al. Combined sugar yields for dilute sulfuric acid pretreatment of corn stover followed by enzymatic hydrolysis of the remaining solids. Bioresource Technology (2005), v96, p. 1967-1977.*
Vaheri et al. Transglycosylation products of the cellulase system of Trichoderma reesei. Biotechnology Letters (1979), v1, p. 41-46.*

* cited by examiner

*Primary Examiner* — Sean C. Barron
(74) *Attorney, Agent, or Firm* — Millen White Zelano and Branigan, PC; John Sopp (57) ABSTRACT

A process for producing oligosaccharides from lignocellulosic biomass, having the following steps:
a) pre-treating the biomass in a pre-treatment reactor (1) in order to provide an effluent containing a pre-treated substrate;
b) enzymatic hydrolysis of the pre-treated substrate contained in the effluent from step a) in a reactor, in the presence of cellulases such that a hydrolysate containing glucose, cellulases and water is produced;
c) removing at least a portion of the hydrolysate from step b) comprising a liquid fraction;
d) reducing the water content of said portion of the hydrolysate in step c) such that the liquid fraction of the hydrolysate has a water content of less than 65% by weight with respect to the total weight of the liquid fraction;
e) incubating the hydrolysate from step d) at a temperature in the range 40° C. to 70° C. for the time necessary to produce an effluent enriched in oligosaccharides.

13 Claims, 4 Drawing Sheets

PROCESS FOR THE PRODUCTION OF OLIGOSACCHARIDES FROM LIGNOCELLULOSIC BIOMASS

The present invention falls within the context of a process for the production of oligosaccharides from lignocellulosic biomass. The invention also relates to a process for the production of cellulases incorporating a unit for the production of oligosaccharides synthesized from lignocellulosic biomass. Finally, the present invention relates to a process known as a "second generation" process for the production of sugars and alcohols, solvents or organic acids from lignocellulosic biomass and which comprises a unit for the in-situ production of oligosaccharides and cellulases.

PRIOR ART

In order to meet the challenges of energy transition, and in particular to reduce the impact of modes of transport on the environment and their dependence on oil, many studies are in the process of being carried out in order to use and optimize renewable bioresources such as lignocellulosic biomass.

Lignocellulosic biomass represents one of the most abundant renewable resources on Earth. The substrates under consideration vary widely, since they concern both woody substrates (hardwood and softwood), agricultural by-products (straw) and those from industries generating lignocellulosic waste (agroalimentary industry, papermaking industry).

Lignocellulosic biomass is composed of three principal constituents: cellulose (35% to 50%), hemicellulose (23% to 32%), which is a polysaccharide essentially constituted by pentoses and hexoses, and lignin (15% to 25%), which is a macromolecule with a complex structure and a high molecular weight deriving from the copolymerization of phenylpropenoic alcohols. These various molecules are responsible for the intrinsic properties of the plant wall and are organized into a complicated matrix.

Cellulose, which is in the majority in this biomass, is thus the most abundant polymer on Earth and that which has the greatest potential for forming materials and biofuels. However, the potential of cellulose and its derivatives has not so far been fully exploited, mainly because extracting the cellulose is difficult. In fact, this step is made difficult by the structure of the plants themselves. The main technological stumbling blocks identified for extraction and transformation of cellulose are its accessibility, its crystallinity, its degree of polymerization and the presence of hemicellulose and lignin.

The principle of the process for the conversion of lignocellulosic biomass using biotechnological processes uses a step for enzymatic hydrolysis of cellulose contained in the plant material in order to produce glucose. The glucose obtained may then be fermented into various products such as alcohols (ethanol, 1,3-propanediol, 1-butanol, 1,4-butanediol etc.) or acids (acetic acid, lactic acid, 3-hydroxypropionic acid, fumaric acid, succinic acid, etc.).

Cellulose and possibly hemicelluloses are the targets for enzymatic hydrolysis, but they are not directly accessible to enzymes. For this reason, these substrates have to undergo a pre-treatment preceding the enzymatic hydrolysis step. The pre-treatment is intended to modify the physical and physico-chemical properties of the lignocellulosic material with a view to improving accessibility to the cellulose trapped in the lignin and hemicellulose matrix.

Hydrolysis is a difficult operation which generally involves an enzymatic type hydrolysis. This latter is in fact recommended, as it generates few effluents to be processed, compared with a chemical type hydrolysis (for example acid hydrolysis).

Currently, hydrolysis of this type is carried out in the presence of cellulases which are produced from microorganisms such as bacteria or fungi (*Clostridium, Aspergillus, Trichoderma*).

These microorganisms produce a cocktail of enzymes which act in a synergistic manner to hydrolyse the cellulose into monomeric glucose and also possibly hemicellulose. Of particular note in the family of enzymes present are the endoglucanases, exoglucanases and β-glucosidases. Of these, *Trichoderma reesei* is the most promising species because it is capable of secreting large quantities of highly active cellulases.

However, the cost of producing cellulases remains high and represents one of the economic obstacles to implementing processes of this type on an industrial scale.

Industrially, the optimized production of cellulases by *Trichoderma reesei* is carried out in a fed-batch protocol (infeed without withdrawal) using a feed solution containing lactose as the sugar inducing the production of cellulases (FR 2 555 603). However, lactose used alone is too expensive to permit a low-cost production of cellulases.

In order to reduce the cost associated with the purchase of lactose, it is possible to envisage replacing all or a portion of the lactose inducing fraction by another inducing sugar which would be:
 either as good an inducer but less expensive
 or more expensive but a better inducer, which would mean that the minimum quantity of inducer in the feed solution for the fed-batch protocol could be further reduced.

Thus, for example, cellobiose (β(1→4) glucose dimer) is a natural inducer for the production of cellulases in *Trichoderma reesei*. Cellobiose is the last intermediate in the hydrolysis of cellulose to glucose which is catalysed by the enzyme β-glucosidase. In order to produce cellobiose, it might be possible to consider using a cocktail of cellulases which is free from β-glucosidases in order to hydrolyse the cellulose to cellobiose. However, the kinetics of this reaction are slow, because cellulases (cellobiohydrolase and endoglucanase) are very strongly inhibited by cellobiose. Furthermore, such an option would necessitate the separate production of a specific cocktail which was free of β-glucosidase, which would make it less profitable industrially. Another alternative might consist of using sophorose (β(1→2) glucose dimer) which is known to be a stronger inducer, but its cost would still be prohibitive for the purposes of industrial use.

Thus, one aim of the invention is to propose processes for the production of sugars, cellulases and alcohol and/or solvents which are optimized from the point of view of operating costs, in particular starting from lignocellulosic biomass.

SUMMARY OF THE INVENTION

In a first aspect, the invention proposes a process for the production of oligosaccharides from lignocellulosic biomass, comprising at least the following steps:
 a) pre-treating the biomass in a pre-treatment reactor in order to provide an effluent containing a pre-treated substrate;

b) carrying out an enzymatic hydrolysis of the pre-treated substrate contained in the effluent obtained from step a) in a reactor, in the presence of cellulases in a manner such that a hydrolysate containing glucose, cellulases and water is produced;

c) removing at least a portion of the hydrolysate obtained from step b) comprising a liquid fraction;

d) reducing the water content of said portion of the hydrolysate removed in step c) in a manner such that the liquid fraction of the hydrolysate has a water content of less than 65% by weight of water with respect to the total weight of the liquid fraction of the hydrolysate;

e) incubating the hydrolysate obtained from step d) at a temperature in the range 40° C. to 70° C. for the time necessary to produce an effluent enriched in oligosaccharides.

The process for the production of oligosaccharides of the invention uses lignocellulosic biomass as the starting material, which is readily accessible and which is also cheap.

The inventors have observed that it is possible to promote the formation of oligosaccharides starting from a hydrolysate containing glucose and cellulases by incubation when the water content of the liquid fraction of the hydrolysate is less than or equal to 65% by weight with respect to the total weight of the liquid fraction of the hydrolysate.

Preferably, the hydrolysate obtained from the hydrolysis step which is incubated has a β-glucosidase activity of at least 1 IU/mL, and preferably at least 5 IU/mL. This β-glucosidase activity is measured by using as a substrate 5 mM pNPG (para-nitrophenol-β-glucopyranose) in a 50 mM citrate buffer at a pH of 4.75, with incubation for 30 minutes at 50° C. [Dashtban, Maki, Leung, Mao, and Qin (2010) *Cellulase activities in biomass conversion: Measurement Methods and Comparison. Critical Reviews in Biotechnology* 30 (4) pages 302-309]. Next, the concentration of para-nitrophenol, produced by the hydrolysis of pNPG by β-glucosidase, is measured by absorbance. The β-glucosidase activity is expressed in IU/mL, where IU signifies μmol/min (for μmol of product liberated per minute of reaction).

In accordance with one embodiment, step d) for reducing the water content of the liquid fraction of the hydrolysate is carried out by evaporation at a temperature of less than 90° C.

In accordance with another embodiment, step d) for reduction of the water content of the liquid fraction of the hydrolysate is carried out by adding glucose to the hydrolysate removed in step c).

Alternatively, in step d), the hydrolysate removed in step c) is separated into at least a first portion and a second portion, the first portion of the hydrolysate is concentrated at a temperature of more than 90° C. in order to obtain a concentrated hydrolysate portion and the concentrated hydrolysate is mixed with the second, non-concentrated hydrolysate portion.

In accordance with another embodiment, in step d), a membrane separation of the hydrolysate removed in step c) is carried out, for example by reverse osmosis or by nanofiltration, in order to recover a hydrolysate with a reduced water content and an aqueous solution.

In the context of the process for the production of oligosaccharides in accordance with the invention, it is also possible to carry out a solid/liquid separation of the effluent obtained from step a) in order to recover a liquid fraction containing sugars and a solid fraction containing the pre-treated substrate which is sent to step b). Regarding the liquid fraction, this may either be treated as a mixture with the hydrolysate in step d), or be mixed with the effluent enriched in oligosaccharides obtained from step e).

Preferably, at the end of incubation step e), an effluent is obtained comprising oligosaccharides selected from sophorose and gentiobiose, alone or as a mixture.

The process for the production of oligosaccharides in accordance with the invention may itself be integrated into an existing unit for the production of alcohol and/or solvents, known as second generation, which uses lignocellulosic biomass as the starting material.

Thus, the invention also concerns a process for the production of cellulases starting from lignocellulosic biomass, comprising at least the following steps:

a) pre-treating the biomass in a pre-treatment reactor in order to provide an effluent containing a pre-treated substrate;

b) carrying out an enzymatic hydrolysis of the pre-treated substrate contained in the effluent obtained from step a) in a reactor, in the presence of cellulases in a manner such that a hydrolysate containing glucose, cellulases and water is produced;

c) removing at least a portion of the hydrolysate obtained from step b) comprising a liquid fraction;

d) reducing the water content of said portion of the hydrolysate removed in step c) in a manner such that the liquid fraction of the hydrolysate has a water content of less than 65% by weight of water with respect to the total weight of the liquid fraction of the hydrolysate;

e) incubating the hydrolysate obtained from step d) at a temperature in the range 40° C. to 70° C. for the time necessary to produce an effluent enriched in oligosaccharides;

f) sending at least a portion of the hydrolysate enriched in oligosaccharides to a reactor containing a culture medium and microorganisms which are capable of producing cellulases; and g) culturing the mixture in order to produce an effluent enriched in cellulases.

In accordance with the invention, the effluent obtained from step e) containing oligosaccharides is used as an inducing solution in a unit for the production of cellulases.

The invention also pertains to a process for the production of alcohols, solvents or organic acids, by themselves or as a mixture, which comprises the steps of the process for the production of cellulases described above and supplemental steps in which a portion of the hydrolysate obtained from step b) is sent to a fermentation reactor comprising microorganisms in order to produce a fermentation must comprising alcohols, solvents or organic acids, alone or as a mixture, and at least a portion of the effluent enriched in cellulases obtained from step g) is recycled to the reactor of step b).

Alternatively, the process for the production of alcohols, solvents or organic acids of the invention, alone or as a mixture, may implement a step in which a portion of the effluent obtained from step a) is sent to a unit for simultaneous hydrolysis and fermentation in order to produce alcohols and/or solvents, and at least a portion of the effluent enriched in cellulases obtained from step g) is recycled to a simultaneous hydrolysis and fermentation unit.

As an example, the fermentation of the invention can be used to produce ethanol as the major alcohol or n-butanol, alone or as a mixture with acetone or isopropanol.

The process for the production of alcohol and/or solvents of the invention comprises a step for the in-situ production of cellulases starting from oligosaccharides which are themselves synthesized in-situ from sugars already present in the process.

The process for the production of alcohol, solvents or organic acids, by themselves or as a mixture, of the invention have the advantage that carrying it out dispenses with the costs of purchasing, transporting and storing oligosaccharides (used as the inducers) necessary for the production of the cellulases as, because of the process, the oligosaccharides are produced in-situ starting from sugars which are already available within the process.

BRIEF DESCRIPTION OF THE FIGURE

Other characteristics and advantages of the invention will be better understood and will become clearer from the following description made with reference to the drawings in which.

In general, similar elements are denoted by identical reference numerals in the figures.

DETAILED DESCRIPTION OF THE INVENTION

Figure 1:
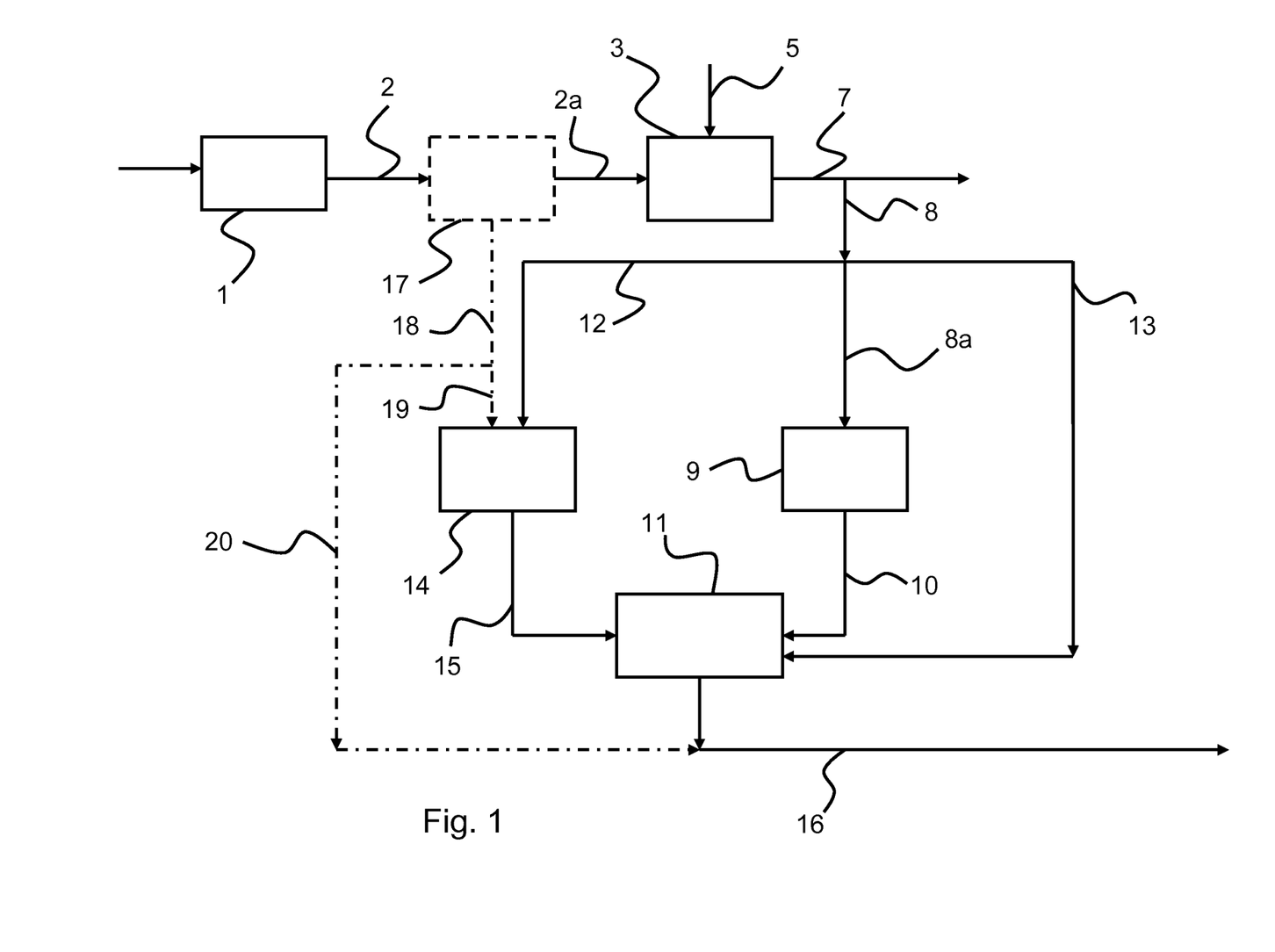
FIG. 1 is a diagrammatic representation of an embodiment of the process for the production of oligosaccharides in accordance with the invention.

Referring to FIG. 1, the process for the production of oligosaccharides in accordance with the invention comprises a step for pre-treatment of the biomass prior to the enzymatic hydrolysis step, carried out in a pre-treatment reactor 1. The aim of pre-treatment is to render the cellulose and optionally the hemicelluloses accessible to the enzymes. In particular, pre-treatment is intended to modify the physical and physico-chemical properties of the lignocellulosic material, with a view to improving accessibility to the cellulose trapped within the matrix of lignin and hemicellulose.

A large number of technologies exist for carrying out this pre-treatment. Examples which may be cited are acid digestion, alkaline digestion, steam explosion, Organosolv processes, etc. The efficiency of the pre-treatment is measured both by the material balance at the end of the pre-treatment (degree of recovery of sugars in the form of monomers or soluble oligomers or insoluble polymers) and also by the susceptibility of the cellulosic and hemicellulosic residues to enzymatic hydrolysis.

Preferably, pre-treatment by explosion with steam, also known as "steam explosion", "steam gunning", "explosive decompression" and "steam pre-treatment", is used, which is distinguished by its performance in terms of degradability of the cellulose and its low degree of dilution. In this process, the biomass is heated rapidly to a high temperature (150° C.-250° C.) by injecting steam under pressure. The treatment is generally stopped by a sudden decompression, known as decompression or explosion, which breaks down the lignocellulosic matrix. The dwell times vary from 10 seconds to several minutes for pressures of 10 to 50 bar. This technique is carried out either in batches or continuously. Certain technologies propose injecting water in order to cool the medium before decompression.

Steam explosion may be preceded by an acid impregnation in order to increase hydrolysis of the hemicelluloses during boiling. When steam explosion is applied to a substrate which has already been acidified, for example with $H_2SO_4$, it results in dissolution and almost complete hydrolysis of the hemicelluloses into their monomers, while limiting degradation into furfural. Furthermore, the susceptibility of the cellulose to enzymatic hydrolysis is improved. The use of an acid catalyst means that the temperature of the process can be reduced (150° C. to 200° C. as opposed to 250° C. for steam explosion with no catalyst), and thus the formation of degradation compounds can be minimized. Steam explosion can also be preceded by a step for acid boiling which is aimed at hydrolysing the hemicelluloses and withdrawing them in a liquid solution in the form of monomeric and/or oligomeric sugars.

The effluent comprising the pre-treated biomass is withdrawn via a line 2 and is treated in an enzymatic hydrolysis reactor 3 in order to obtain sugars which can be fermented by the action of cellulases on the cellulose which has been rendered accessible by the pre-treatment step. As can be seen in FIG. 1, the cellulases are introduced into the unit via the line 5. Preferably, the cellulases which can be used for the conversion of cellulose into monomeric sugars (for example glucose) form part of a multi-enzymatic system which generally comprises:

endoglucanases (EG) which cleave the cellulose randomly at amorphous zones of the cellulose;
  exoglucanases which act progressively on the free ends of the cellulose chains;
  β-glucosidases, which in particular hydrolyse cellodextrins and cellobiose into glucose. The conditions for enzymatic hydrolysis, principally the dry matter content of the mixture to be hydrolysed (determined using the ASTM method E1756-01) and the quantity of enzymes used are selected such that in the range 20% to 99%, preferably in the range 30% to 95% by weight of the cellulose with respect to the total weight of the cellulose is dissolved in a manner such that a hydrolysate containing monomeric sugars including glucose in particular is provided. The water necessary for obtaining the target dry matter content is added to the reactor 3 via a line (not shown). The desired dry matter content is generally in the range 5% by weight to 45% by weight, preferably in the range 8% by weight to 40% by weight. The enzymatic hydrolysis is preferably carried out at a pH in the range 4 to 5.5 and at a temperature in the range 40° C. to 60° C. The necessary additives, for example nutrients, chemical reagents such as sodium hydroxide and/or ammonia and/or potassium hydroxide, are introduced via a line (not shown) which is dedicated to this purpose.

The hydrolysate obtained from the enzymatic hydrolysis reactor comprises a liquid fraction containing water, a mixture of monomeric sugars including glucose, an enzymatic cocktail and a solid fraction comprising non-hydrolysed solid materials (including lignin). Preferably, the hydrolysate which is used in the remainder of the process has a β-glucosidase activity of at least 1 IU/mL, preferably at least 5 IU/mL. Generally, the water content of the liquid fraction of the hydrolysate obtained from the hydrolysis step is in the range 85% to 95% with respect to the total weight of the liquid fraction of the hydrolysate.

As indicated in FIG. 1, the hydrolysate is evacuated from said reactor 3 via the line 7 and a portion (or fraction) of the hydrolysate is sent via the line 8 to a treatment unit which can be used to reduce the water content of the liquid fraction of the hydrolysate in order to bring this content to a value of 65% by weight or less with respect to the total weight of the liquid fraction, preferably less than 60% by weight, and more preferably less than 50%.

The water content of the liquid fraction of the hydrolysate is determined by filtering a sample of hydrolysate over a filtering medium with a porosity of 1.2 μm in order to recover a liquid fraction. Said liquid fraction then undergoes a test in accordance with ASTM standard E1756-01 which consists of measuring the loss of weight of the liquid fraction by drying at 105° C. until the residue is of constant weight. The weight lost during drying then corresponds to the weight of water initially present in the sample and the remaining weight corresponds to the solid materials and soluble materials contained in the liquid fraction.

The step for reducing the water content may be carried out using any of the concentration techniques which are known to the skilled person such as, for example, by membrane separation (for example reverse osmosis, nanofiltration), by evaporation of a portion of the water, or by liquid-liquid extraction. In a variation, which is not shown, the water content is reduced by mixing the hydrolysate with a more concentrated solution of sugars such as a glucose syrup, for example.

Preferably, the concentration treatment involves at least one step for evaporating water. Three embodiments will be detailed now with reference to FIG. 1.

In a first preferred embodiment, this step for reduction of the water content of the hydrolysate is carried out in an evaporator in order to extract water and thus to concentrate the hydrolysate in sugars. At least a portion of the hydrolysate removed from the hydrolysis reactor 3 is sent to an evaporator 9 via the line 8, 8a in order to evaporate off the water. This evaporation is carried out by heating the hydrolysate to a temperature of less than 90° C., preferably in the range 40° C. to 70° C., under atmospheric pressure or under vacuum. The temperature employed is selected in a manner such that the cellulases present in the hydrolysate and which are useful for the following incubation operation, which will be explained below, are not denatured. The water-depleted effluent obtained from the evaporator 9 is then transferred to an incubation reactor 11 via the line 10.

In accordance with a second embodiment, as indicated in FIG. 1, the hydrolysate which is removed via the line 8 is divided into two streams, via lines 12 and 13 respectively. The stream of hydrolysate withdrawn via the line 12 is sent to an evaporator 14, which is operated at a temperature of more than 90° C., in order to extract water and thus concentrate the hydrolysate in sugars and in particular in glucose. At the end of the evaporation step, the hydrolysate is sent to the incubator 11 by means of the line 15. Regarding the stream of hydrolysate withdrawn via the line 13, this is sent directly to the incubator 11 in order to supply the cellulases necessary for the conversion of glucose into oligosaccharides.

In accordance with a third embodiment, which combines the first two embodiments described above, the hydrolysate which is extracted via the line 8 is divided into three streams which are sent to the evaporator 9, the evaporator 14 and the incubator 11 via lines 8a, 12 and 13 respectively.

In accordance with the invention, the process for the production of oligosaccharides comprises a step for incubation of the hydrolysate the liquid fraction of which comprises a water content of 65% by weight or less. The aim of this step is to carry out the conversion of at least a portion of the glucose to oligosaccharides with the properties of inducing the expression of genes coding for cellulases in fungi. In particular, the incubation step can be used to produce sophorose, a dimer of molecules of glucose connected via a β-1-2 linkage, and/or gentiobiose, a dimer of glucose molecules connected via a β-1-6 linkage. Preferably, the solution of oligosaccharides contains a mixture of sophorose and gentiobiose at a total concentration (sophorose+gentiobiose) which is generally less than 30 g/L. These two oligosaccharides (or disaccharides) are powerful inducers of the secretion of cellulases in filamentous fungi, in particular in *Trichoderma reesei*.

This incubation step consists of heating the hydrolysate to a temperature in the range 40° C. to 70° C., preferably in the range 50° C. to 65° C., for a period in the range 0.1 to 100 hours, preferably for at least 24 hours, and highly preferably in the range 24 to 72 hours.

At the end of the incubation step, an aqueous solution comprising oligosaccharides is withdrawn from the incubator 11 via the line 16.

In accordance with an alternative embodiment of the process for the synthesis of oligosaccharides (not shown in FIG. 1), the hydrolysate which is withdrawn via the line 8 is treated in a solid/liquid separation unit from which a solid fraction and a liquid hydrolysate fraction containing glucose and cellulases is withdrawn. The liquid fraction of the hydrolysate is then treated in accordance with one of the three embodiments described above, in a manner such that its water content is reduced prior to the incubation step. This solid/liquid separation step may employ one of the following techniques: centrifuging, draining, pressing, filtration and settling.

Referring to FIG. 1, the process of the invention may comprise an optional step for solid/liquid separation using the unit 17, carried out on the effluent obtained from the pre-treatment reactor. This step can thus be used to extract:

a liquid fraction containing sugars obtained from hemicellulose (for example xylose, arabinose, galactose and mannose) via the line 18; and a fraction containing solids (pre-treated biomass) which is sent to the hydrolysis reactor 3 via the line 2a.

In accordance with FIG. 1, all or a portion of the liquid fraction 18 is either mixed directly with the effluent obtained from the incubator 11 via the line 20, or is sent via the line 19 to the evaporator 14, alone or as a mixture with the hydrolysate obtained from the hydrolysis step in order to evaporate off the water, or (via a line which is not shown) to the evaporator 9, alone or mixed with the hydrolysate.

In accordance with the invention, in order to reduce the water content in the hydrolysate, another method may be implemented, as an alternative to or as a complement to those described above, which consists of adding sugar to the hydrolysate.

Figure 2:
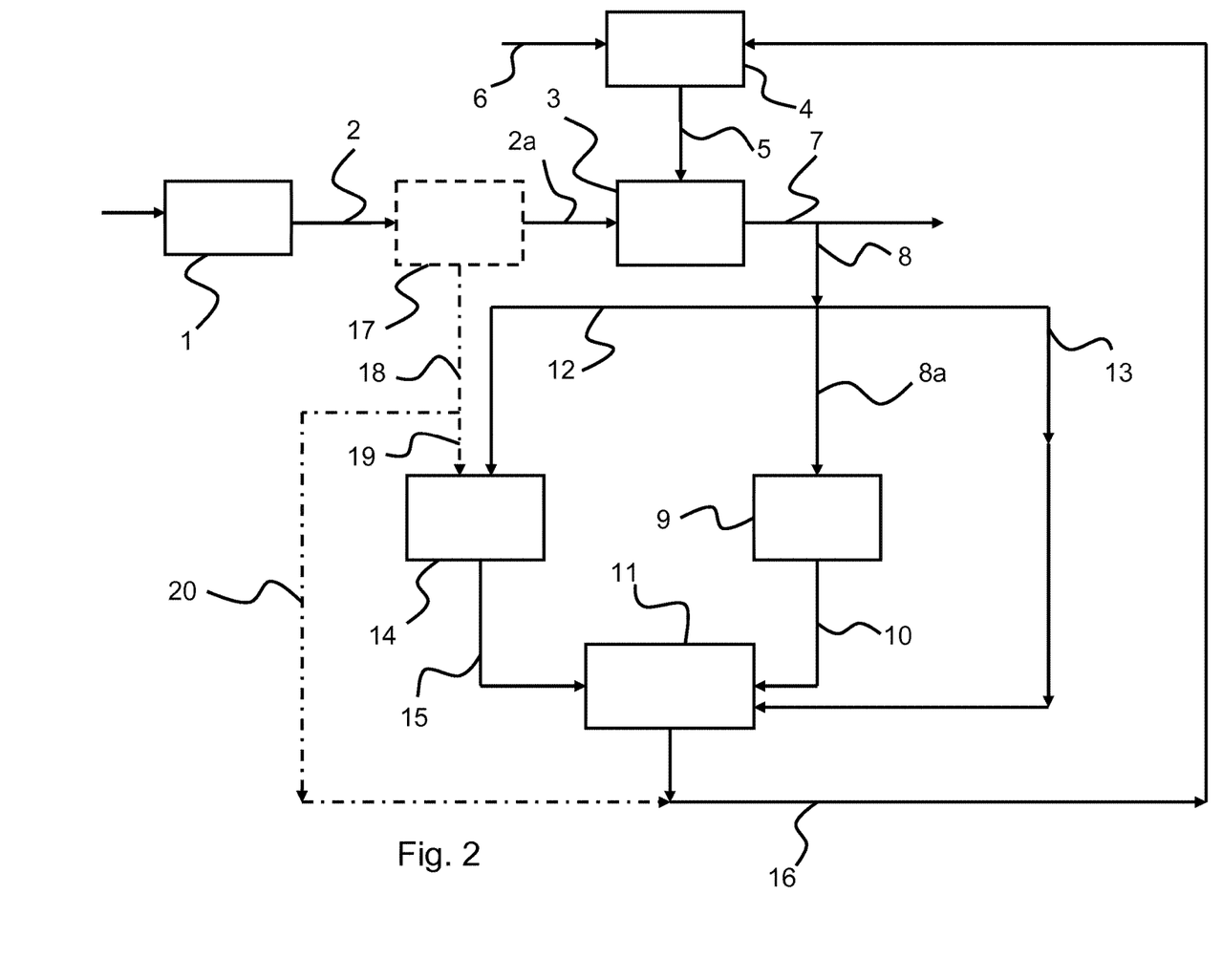
FIG. 2 is a diagrammatic representation of an embodiment of the process for the production of cellulases in accordance with the invention.

Referring to FIG. 2, in addition to the steps already described above, the process for the production of cellulases in accordance with the invention implements a step for the production of cellulases using a fermenter 4 and which uses oligosaccharides which are synthesized in-situ. The production of enzymes is carried out in the fermenter 4 by means of a microorganism which is supplied via the line 6. The microorganisms are preferably selected from cellulolytic bacteria belonging to the genus *Ruminococcus, Clostridium, Cellulomonas, Thermonospora, Streptomyces* or from cellulolytic fungi from the genus *Aspergillus, Penicillium* or *Trichoderma*. Of these, *Trichoderma reesei* is the preferred species because it is capable of secreting large concentrations of highly active cellulases.

As can be seen in FIG. 2, all or a portion of the effluent which is extracted from the incubator 11 via the line 16 is sent to the fermenter 4.

These strains are cultured in stirred and aerated fermenters under conditions which are compatible with their growth and the production of enzymes. It is possible to use any type of production process which is suitable for the microorganism which is known to the skilled person. In particular, it is possible to use a "fed-batch" type process as described in document FR 2 555 603.

To this end, a pre-culture is prepared containing the microorganism and a culture medium comprising the usual mineral salts and vitamin complements and a source of carbon and of energy, preferably in the form of soluble sugars (for example lactose, glucose, xylose or arabinose). The pre-culture is then transferred to a fermenter for the production of enzymes which comprises a culture medium containing at least one sugar and supplemented in a regular manner with the oligosaccharide-inducing solution. Next, enzymes are produced in the fermenter by maintaining the necessary contact between the microorganism and the culture medium and by regularly feeding in the oligosaccharide-inducing solution (for example continuously).

The aqueous solution containing the inducer oligosaccharides is injected, after exhaustion of the initial carbon source, in a regular manner or continuously in order to feed in an optimized quantity in the range 35 to 135 mg of total sugars (containing the inducer oligosaccharides) per gram of cells per hour, preferably in the range 35 to 45 mg.

As indicated in FIG. 2, all or a portion of the fermentation must containing the cellulases of interest is withdrawn from the fermenter 4 via the line 5 in order to supply the hydrolysis reactor 3.

Figure 3:
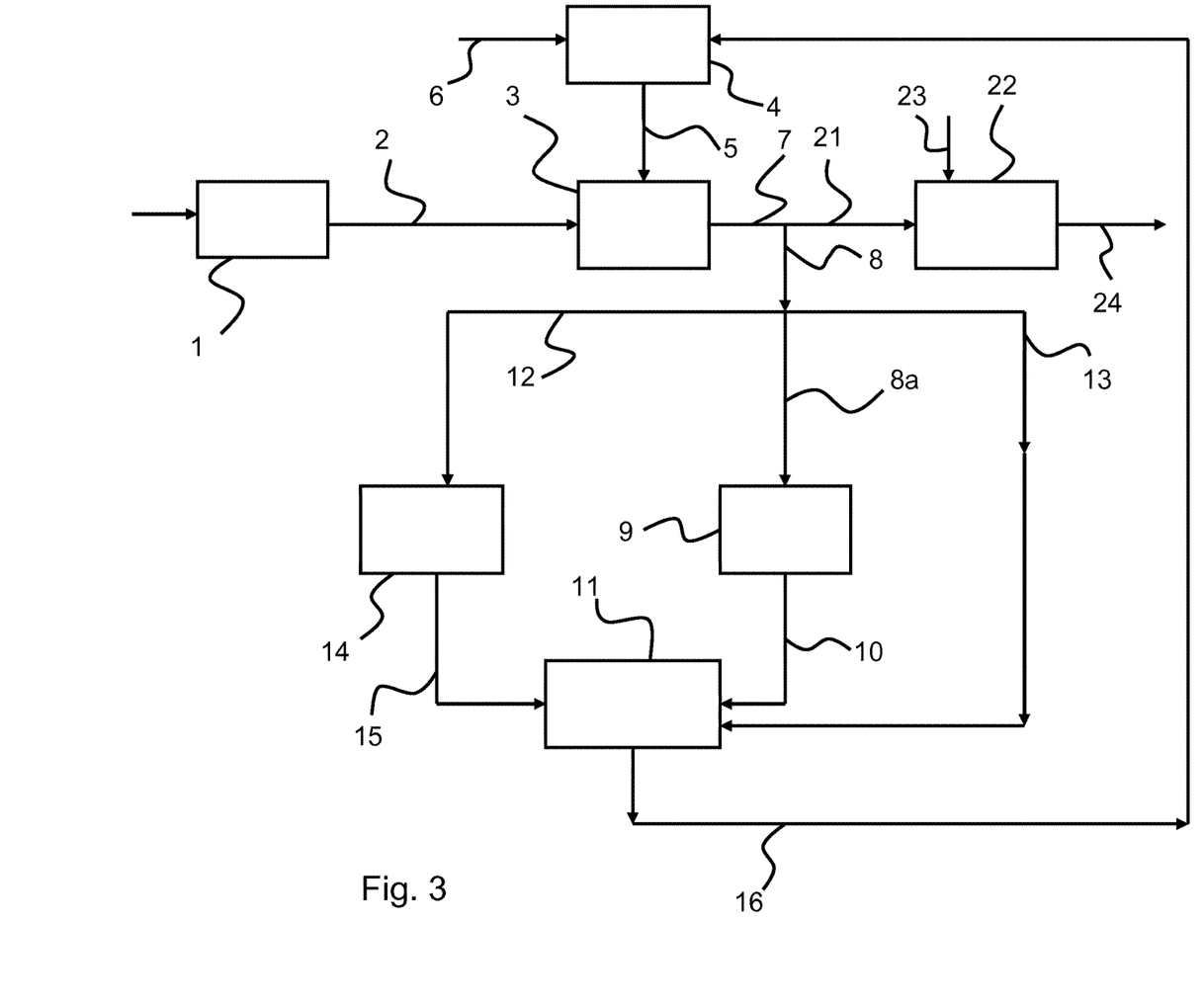
FIG. 3 is a diagrammatic representation of a first embodiment of the process for the production of alcohols and/or solvents in accordance with the invention.

FIG. 3 is a representation of an embodiment of the process for the production of alcohols, solvents or organic acids incorporating a unit for the production of cellulases using oligosaccharides produced from a stream which is internal to the process.

Referring to FIG. 3, the fraction (or portion) of the hydrolysate which is not used for the in-situ synthesis of oligosaccharides is sent via the line 21 to a unit 22 for fermenting sugars present in the hydrolysate.

In the fermentation unit 22, the hydrolysate is brought into contact with one or more fermentation microorganisms introduced via the line 23. The fermentable sugars are thus transformed into alcohols, solvents or organic acids, by themselves or as a mixture, by the microorganisms. The fermentation step in the unit 22 may be carried out at a temperature in the range 30° C. to 40° C. and at a pH in the range 3 to 6.5. At the end of the fermentation step, a fermentation must is obtained, which is evacuated from the unit 22 via the line 24 and comprises material in suspension and a liquid phase containing the desired product or products (alcohols and/or solvents).

The must obtained from the fermentation unit 22 is introduced via the line 24 into a separation unit (not shown) which can be used to separate the must into different products: alcohols and/or solvents, a liquid stillage containing non-fermented sugars and a solid residue principally containing lignin, as well as cellulose and hemicellulose which have not been hydrolysed.

As an example, the fermentation may be of the type:
a) "ethanolic" type, which corresponds to the production of ethanol as the major alcohol by means of yeasts (for example *S. cerevisiae*) or bacteria (for example *Z. mobilis*) or other microorganisms.
b) "butylic" type, which itself here includes:
   a fermentation producing n-butanol alone;
   an "ABE" fermentation, which corresponds to the production of a mixture comprising acetone, n-butanol (major product), and ethanol. Traces of isopropanol may also be present;
   an "IBE" fermentation, which corresponds to the production of isopropanol, n-butanol (major product) and ethanol.
   These fermentations are generally carried out using a microorganism of the genus *Clostridium* and are carried out under strict anaerobiosis;
   an "isobutylic" type fermentation, which in general corresponds to the production of isobutanol alone. Numerous microorganisms, all genetically modified, are capable of carrying out this conversion (for example *E. coli, Corynebacterium, S. cerevisiae*) using an amino acid pathway;
c) "propylic" type, which corresponds to the production of propanol or isopropanol.

Figure 4:
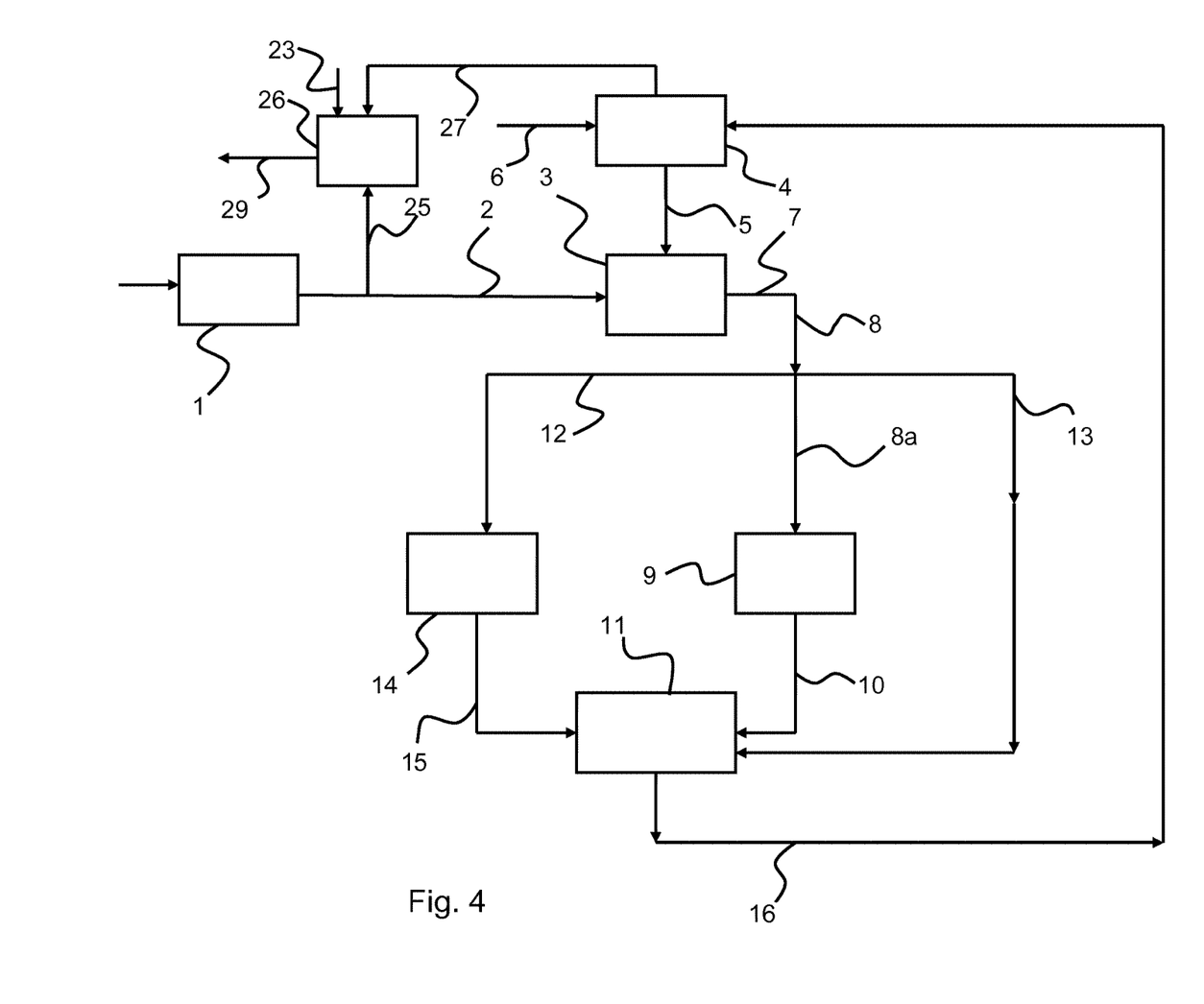
FIG. 4 is a diagrammatic representation of a second embodiment of the process for the production of alcohols and/or solvents in accordance with the invention.

In accordance with one embodiment of the process for the production of alcohol and/or solvent incorporating a unit for the production of cellulases using oligosaccharides produced from a stream which is internal to the process, the fermentation of sugars into alcohols and/or solvents is carried out in a manner concomitant with the enzymatic hydrolysis step ("SSF" embodiment, *Simultaneous Saccharification and Fermentation*). Referring to FIG. 4, the effluent obtained from the pre-treatment unit 1 is divided into two streams via the lines 2 and 25. The stream 2 containing the pre-treated biomass is sent to the unit for the in-situ production of cellulase as described for FIG. 2. The stream 25 is transferred to the SSF fermentation unit 26 which simultaneously carries out:
   hydrolysis of cellulose due to the cellulases supplied via the line 27 deriving from the unit for the in-situ production of cellulases 4; and
   fermentation of the fermentable sugars liberated during the enzymatic hydrolysis by means of the microorganisms which are introduced via the line 23.

When the enzymatic hydrolysis and the alcoholic fermentation are carried out in one and the same operation (SSF process), the temperature is generally in the range 30° C. to 45° C., and the pH is in the range 4 to 6.

It should be pointed out that it is entirely possible to combine the embodiments described in relation to the process for the production of oligosaccharides and cellulases in the context of the process for the production of alcohols and/or solvents of the present invention.

EXAMPLES

The abbreviation "DM" will be used hereinafter for the dry matter (solids and solubles) present in a medium. The quantity of dry matter (or "Total Solids") is determined in accordance with the ASTM method E1756-01 which consists of a loss of weight at 105° C. until a constant weight is obtained.

Example 1

Not in Accordance

An enzymatic hydrolysis of straw pre-treated by acid digestion was carried out in a medium comprising 15% by weight of DM (15 g dry matter of straw per 100 g of total mass) using a cocktail of cellulases produced by

*Trichoderma reesei*. The quantity of cellulases used for the hydrolysis was fixed at 10 mg of cellulases per gram of dry matter (DM). The mixture was hydrolysed at a temperature of 50° C., with stirring for 72 hours. At the end of the hydrolysis, a crude hydrolysate was recovered which had a glucose concentration of 75 g/L, and a β-glucosidase activity of 10 IU/mL. Furthermore, the liquid fraction had a water content of 92% by weight with respect to the weight of the liquid fraction.

The crude hydrolysate was then incubated for 24 hours at 50° C., with stirring. At the end of the incubation phase, the hydrolysate was boiled for 5 minutes in order to denature the enzymes, then analysed by HPLC. The analysis indicated that the hydrolysate did not contain oligosaccharides.

Example 1, not in accordance with the invention, showed that incubating a hydrolysate with a water content of more than 65% by weight could not transform at least a portion of the glucose into oligosaccharides, and in particular into sophorose and/or gentiobiose.

Example 2

In Accordance with the Invention

The crude hydrolysate obtained in Example 1 was supplemented with a 60% by weight glucose syrup in order to obtain a liquid fraction with a concentration of glucose of 500 g/L and a water content of 57.5% by weight of water with respect to the total weight of the liquid hydrolysate fraction. The mixture was incubated for 24 hours at 50° C., with stirring. At the end of the incubation phase, the mixture was boiled for 5 minutes in order to denature the enzymes, then analysed by HPLC. The hydrolysate obtained contained 22 g/L of a mixture of sophorose and gentiobiose and 477 g/L of glucose (i.e. 4.4% conversion of glucose into oligosaccharides).

Example 3

In Accordance with the Invention

The crude hydrolysate obtained in Example 1 was filtered using a filter with a porosity of 100 μm in order to separate:
- a liquid fraction containing 12% by weight of dry matter (DM);
- a solid fraction containing 35% by weight of dry matter (DM).

The liquid fraction contained 75 g/L of glucose and had a β-glucosidase activity of 6 IU/mL and a water content of approximately 90% by weight.

The liquid fraction was then supplemented with a 60% by weight glucose syrup in order to obtain a liquid fraction with a concentration of glucose of 500 g/L and a water content of 57.5% by weight. The mixture was incubated for 24 hours at 50° C., with stirring. At the end of the incubation phase, the mixture was boiled for 5 minutes in order to denature the enzymes, then analysed by HPLC. The analysis indicated that the hydrolysate obtained contained approximately 11 g/L of a mixture of sophorose and gentiobiose and 488 g/L of glucose (i.e. 2.2% of conversion of glucose into oligosaccharides).

Example 4

In Accordance with the Invention

An aqueous solution containing 300 g/L of glucose, 300 g/L of xylose and 10 IU/mL of β-glucosidase activity and with a water content of approximately 50% by weight was prepared. This solution was incubated for 24 hours at 50° C., with stirring. After incubation, the mixture was boiled for 5 minutes in order to denature the enzymes, then analysed by HPLC. The hydrolysate thus contained 21 g/L of a sophorose and gentiobiose mixture (i.e. 7% conversion of glucose into oligosaccharides), 278 g/L of glucose and 300 g/L of xylose.

Examples 2 to 4 of the invention show that it is possible to produce oligosaccharides by incubation of a lignocellulosic biomass hydrolysate when its liquid fraction has a water content of less than 65% by weight with respect to the total weight of the liquid fraction.

Example 4 also indicates that it is possible to replace at least a portion of the glucose with pentoses in the incubation solution in order to produce inducing oligosaccharides.

Example 5

In Accordance with the Invention

Four Dasgip bioreactors with a useful volume of 750 mL containing a saline medium (5 g/L $KH_2PO_4$, 2.8 g/L $(NH_4)_2SO_4$, 0.6 g/L $MgSO_4.7H_2O$, 0.6 g/L $CaCl_2.2H_2O$, 60 mg/L $FeSO_4.7H_2O$, 13 mg/L $MnSO_4.4H_2O$, 17 g/L $ZnSO_4.7H_2O$, 1 g/L corn steep) and 15 g/L of glucose were sterilized and then inoculated with a preculture of *Trichoderma reesei* in a flask. Throughout the culture, the pH was maintained at 4.8 by adding ammonium hydroxide, $NH_4OH$, or sulphuric acid, $H_2SO_4$. After exhaustion the glucose (after approximately 30 hours), a synthesis of cellulases secreted by *Trichoderma reesei* was carried out in fed-batch mode using aqueous solutions each containing a total quantity of sugars of 250 g/L but with different sugar compositions:
- solution 1 contained only glucose, at a concentration of 250 g/L;
- solution 2 was the liquid fraction of Example 2, diluted with water in a manner such that it contained 11 g/L of the sophorose and gentiobiose mixture and 239 g/L of glucose;
- solution 3 was the liquid fraction of Example 3, diluted with an aqueous solution of 100 g/L glucose, in a manner such that it contained 6 g/L of a sophorose and gentiobiose mixture and 244 g/L of glucose;
- solution 4 contained only lactose, at a concentration of 250 g/L.

The concentration of proteins (cellulases) in the culture medium was measured using Lowry's method [Lowry, Rosenbrough, Farr, Randall (1951) *Protein measurement with the Folin phenol reagent. Journal of Biochemical Chemistry* 193 (1) pages 265-275].

With solution 1, no induction of protein production was observed. The concentration of proteins remained stable at approximately 1 to 2 g/L after 250 hours of culture.

When solutions 2, 3 and 4 (in accordance with the invention) were used for the culture, protein production was observed. After 250 hours of culture, the culture medium contained 35 g/L, 36 g/L and 34 g/L of proteins respectively. The process of the invention can thus be used to produce cellulases by microorganisms, starting from an inducing solution containing a mixture of sophorose and gentiobiose obtained from a hydrolysate of lignocellulosic material.

The invention claimed is:

1. A process for the production of oligosaccharides from lignocellulosic biomass, comprising at least the following steps:

a) pre-treating the biomass in a pre-treatment reactor in order to provide an effluent containing a pre-treated substrate;
b) carrying out an enzymatic hydrolysis of the pre-treated substrate contained in the effluent obtained from step a) in a reactor, in the presence of cellulases, in a manner such that a hydrolysate containing glucose, cellulases and water is produced;
c) removing at least a portion of the hydrolysate obtained from step b) comprising a liquid fraction;
d) reducing the water content of said at least a portion of the hydrolysate removed in step c) in a manner such that the liquid fraction of the resulting hydrolysate has a water content of less than 65% by weight of water with respect to the total weight of the liquid fraction of the at least a portion of the hydrolysate removed in step c);
e) incubating the resulting hydrolysate with reduced water content obtained from step d) at a temperature in the range 40° C. to 70° C. for a time necessary to produce an effluent enriched in oligosaccharides.

2. The process according to claim 1 in which in step d), the at least a portion of the hydrolysate removed in step c) is reduced in water content by evaporation at a temperature of less than 90° C.

3. The process according to claim 1 in which in step d), glucose is added to the at least a portion of the hydrolysate removed in step c).

4. The process according to claim 1 in which in step d), a membrane separation of the at least a portion of the hydrolysate removed in step c) is carried out in order to separate at least a portion of the water of the liquid fraction.

5. The process according to claim 1 in which in step d), the at least a portion of the hydrolysate removed in step c) is separated into at least a first hydrolysate portion and a second hydrolysate portion, the first hydrolysate portion is reduced in water content by evaporation at a temperature of more than 90° C. and this reduced in water first hydrolysate portion is mixed with the second hydrolysate portion.

6. The process according to claim 1, in which a solid/liquid separation of the effluent obtained from step a) is carried out in order to recover a liquid fraction containing sugars and a solid fraction containing the pre-treated substrate, said solid fraction being sent to step b).

7. The process according to claim 6, in which the hydrolysate is treated in step d) as a mixture with the liquid fraction containing sugars obtained from the solid/liquid separation of the effluent obtained from step a).

8. The process according to claim 6, in which the liquid fraction containing sugars obtained from the solid/liquid separation of the effluent obtained from step a) is mixed with the effluent enriched in oligosaccharides obtained from step e).

9. The process according to claim 1, in which the effluent obtained from step e) comprises sophorose and/or gentiobiose.

10. The process according to claim 1, in which the liquid fraction of the at least a portion of the hydrolysate removed in step c), before reducing the water content in step d), has a water content of 85% to 95% by weight of water with respect to the total weight of said liquid fraction.

11. The process according to claim 1, in which in step d), the reducing the water content of said at least a portion of the hydrolysate removed in step c) is such that the liquid fraction of the resulting hydrolysate has a water content of less than 50% by weight of water with respect to the total weight of the liquid fraction of the at least a portion of the hydrolysate removed in step c).

12. The process according to claim 1, in which the pre-treating is conducted by an acid digestion, alkaline digestion, steam explosion or Organosolv process.

13. The process according to claim 1, in which the pre-treating is conducted by a steam explosion process.

* * * * *